(12) United States Patent
Mastrull et al.

(10) Patent No.: US 10,407,648 B2
(45) Date of Patent: Sep. 10, 2019

(54) CLEANSING BARS WITH PHENOXYETHANOL

(71) Applicant: Colgate-Palmolive Company, New York, NY (US)

(72) Inventors: Jeffrey Mastrull, Flemington, NJ (US); Viktor Dubovoy, Cresskill, NJ (US); Laurence Du-Thumm, Princeton, NJ (US); Steven Misner, Verona, NJ (US); David Santos, Edison, NJ (US); Long Pan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 12 days.

(21) Appl. No.: 15/533,074

(22) PCT Filed: Dec. 5, 2014

(86) PCT No.: PCT/US2014/068790
§ 371 (c)(1),
(2) Date: Jun. 5, 2017

(87) PCT Pub. No.: WO2016/089421
PCT Pub. Date: Jun. 9, 2016

(65) Prior Publication Data
US 2018/0079992 A1 Mar. 22, 2018

(51) Int. Cl.
| | |
|---|---|
| *C11D 3/382* | (2006.01) |
| *C11D 3/20* | (2006.01) |
| *A61Q 17/00* | (2006.01) |
| *A61Q 19/10* | (2006.01) |
| *A61K 8/02* | (2006.01) |
| *C11D 3/18* | (2006.01) |
| *C11D 3/37* | (2006.01) |
| *C11D 3/48* | (2006.01) |
| *C11D 9/24* | (2006.01) |
| *C11D 9/26* | (2006.01) |
| *C11D 10/04* | (2006.01) |
| *C11D 17/00* | (2006.01) |
| *A61K 8/31* | (2006.01) |
| *A61K 8/34* | (2006.01) |
| *A61K 8/36* | (2006.01) |
| *A61K 8/92* | (2006.01) |
| *A01N 39/00* | (2006.01) |

(52) U.S. Cl.
CPC ............ *C11D 3/2068* (2013.01); *A01N 39/00* (2013.01); *A61K 8/0216* (2013.01); *A61K 8/31* (2013.01); *A61K 8/34* (2013.01); *A61K 8/342* (2013.01); *A61K 8/361* (2013.01); *A61K 8/922* (2013.01); *A61Q 17/005* (2013.01); *A61Q 19/10* (2013.01); *C11D 3/18* (2013.01); *C11D 3/202* (2013.01); *C11D 3/2079* (2013.01); *C11D 3/2093* (2013.01); *C11D 3/373* (2013.01); *C11D 3/382* (2013.01); *C11D 3/48* (2013.01); *C11D 9/24* (2013.01); *C11D 9/26* (2013.01); *C11D 9/267* (2013.01); *C11D 10/04* (2013.01); *C11D 17/006* (2013.01); *C11D 17/0047* (2013.01)

(58) Field of Classification Search
None
See application file for complete search history.

(56) References Cited

U.S. PATENT DOCUMENTS

| | | | |
|---|---|---|---|
| 5,053,159 A | 10/1991 | Joshi | |
| 5,139,781 A | 8/1992 | Birtwistle et al. | |
| 5,753,245 A * | 5/1998 | Fowler | A61Q 5/02 424/401 |
| 6,248,703 B1 | 6/2001 | Finucane et al. | |
| 6,383,999 B1 | 5/2002 | Coyle et al. | |
| 2009/0004122 A1 | 1/2009 | Modak et al. | |

FOREIGN PATENT DOCUMENTS

| | | |
|---|---|---|
| CN | 1238685 A | 12/1999 |
| EP | 0821936 | 2/1998 |
| RU | 2351309 C2 | 4/2009 |
| RU | 2356940 C2 | 5/2009 |

OTHER PUBLICATIONS

International Search Report and Written Opinion in International Application No. PCT/US2014/068790, dated Sep. 2, 2015.

* cited by examiner

*Primary Examiner* — Necholus Ogden, Jr.

(57) ABSTRACT

A cleansing bar composition comprising at least one cleanser chosen from soap and surfactant; phenoxyethanol; and one or more hydrophobic stabilizing agents, wherein the composition is a solid cleansing bar. Also methods of enhancing the deposition of phenoxyethanol by a cleansing bar comprising the step of pre-mixing phenoxyethanol with one or more hydrophobic deposition aids during manufacturing of the cleansing bar.

16 Claims, No Drawings

CLEANSING BARS WITH PHENOXYETHANOL

BACKGROUND OF THE INVENTION

Antibacterial soaps have become widespread over the last twenty years and are very popular with consumers. It is desired to increase the antibacterial effect of antibacterial agents, such as phenoxyethanol. Unfortunately, due to its high aqueous solubility, phenoxyethanol does not provide a long-lasting antibacterial effect in consumer usage. For example, with traditional hand soap products containing phenoxyethanol, once the consumer has rinsed her hands with water after applying the soap, a significant amount of phenoxyethanol is rinsed away.

Consequently, there is a need for a formulation of a cleansing soap bar containing a safe and effective antibacterial agent, such as phenoxyethanol, in a manner that provides a long-lasting antibacterial effect for the consumer.

BRIEF SUMMARY

The inventors have discovered that when phenoxyethanol is pre-mixed with hydrophobic deposition aids prior to incorporation into cleansing bar compositions, the cleansing bars show significantly enhanced deposition of phenoxyethanol on the skin. This results in a long-lasting antibacterial effect for consumers.

In a first exemplary embodiment, the present disclosure provides a cleansing bar composition comprising:
a) at least one cleanser chosen from soap and surfactant;
b) phenoxyethanol; and
c) one or more hydrophobic stabilizing agents,
wherein the composition is a solid cleansing bar.

In a second exemplary embodiment, the invention provides a method of increasing the deposition of phenoxyethanol on the skin by a cleansing bar, comprising the step of combining phenoxyethanol with one or more hydrophobic deposition aids to form a mixture, adding the resulting mixture to at least one cleanser chosen from soap and surfactant, and forming therefrom a cleansing bar.

Use of a hydrophobic deposition aid to retain phenoxyethanol on skin.

DETAILED DESCRIPTION

Unless otherwise specified, all percentages and amounts expressed herein and elsewhere in the specification should be understood to refer to percentages by weight. As used throughout, ranges are used as shorthand for describing each and every value that is within the range. Any value within the range can be selected as the terminus of the range.

As used herein, the term "cleansing bar" shall include bars for cleansing and personal hygienic use comprising a cleanser chosen from soap and surfactant. The cleansing bar may be a soap bar (soap is the cleanser), syndet (non-soap surfactant is the cleanser), or combar (a mixture of soap and surfactant).

The present disclosure provides cleansing bars containing one or more cleanser components, phenoxyethanol and one or more hydrophobic deposition aids.

In one exemplary embodiment, the present disclosure provides a cleansing bar composition (Composition 1) comprising:
 a) one or more (e.g., at least one) cleanser components;
 b) phenoxyethanol; and
 c) one or more (e.g., at least one) hydrophobic deposition aids.

The present disclosure provides additional exemplary embodiments, including 1.1 Composition 1, wherein the phenoxyethanol comprises from 0.01% to 2% by weight of the composition, e.g., from 0.1% to 1.5%, or e.g., from 0.5% to 1%, or e.g., about 1%.

1.2 Composition 1, wherein the phenoxyethanol comprises from 0.1% to 1.5% by weight of the composition.

1.3 Composition 1, wherein the phenoxyethanol comprises from 0.5% to 1% by weight of the composition.

1.4 Composition 1, wherein the phenoxyethanol comprises about 1% by weight of the composition.

1.5 Any of Compositions 1 or 1.1-1.4, wherein the one or more cleanser components comprise a soap, for example, an alkali metal (e.g., sodium or potassium) or alkylammonium (e.g., mono-, di- or tri-ethanol ammonium) salt of a carboxylic acid.

1.6 Any of Compositions 1 or 1.1-1.5, wherein the one or more soap components comprise an alkali metal (e.g., sodium or potassium) or alkylammonium salt of a fatty acid, e.g., a C8-22 saturated or unsaturated fatty acid, preferably a C10-20 saturated or unsaturated fatty acid.

1.7 Any of Compositions 1 or 1.1-1.6, wherein the one or more soap components comprise an alkali metal salt (e.g., sodium or potassium) or alkylammonium salt of a C8-22 carboxylic acid.

1.8 Any of Compositions 1 or 1.1-1.7, wherein the one or more soap components comprise the alkali metal (e.g., sodium or potassium) or alkylammonium salts of the fatty acids present in a natural vegetable oil, e.g., palm kernel oil, palm oil, coconut oil, olive oil or laurel oil, or in tallow (rendered animal fat).

1.9 Any of Compositions 1 or 1.1-1.8, wherein the one or more soap components comprise the alkali metal salt (e.g., sodium or potassium) of palm oil or coconut oil.

1.10 Any of Compositions 1 or 1.1-1.9, wherein the one or more soap components comprise from 30, 40, 50 or 60%/o by weight of the composition to 70, 80, 85, 90 or 95% by weight of the composition.

1.11 Any of Compositions 1 or 1.1-1.10, wherein the one or more hydrophobic deposition aids comprise at least one material chosen from a material having a water solubility less than 1% by weight, petrolatum, white petrolatum, snow white petrolatum, a vegetable oil, palm oil, palm kernel oil, coconut oil, a seed oil, jojoba oil, jojoba wax, a fat, triglyceride, tallow, shea butter, a glycerol ester of a C8-C22 fatty acid; a glycerol ester of lauric, palmitic, stearic, oleic, linoleic or myristic acid; a C8-C22 fatty alcohol, lauryl alcohol, stearyl alcohol, isostearyl alcohol, oleyl alcohol, cetyl alcohol or myristyl alcohol, a C8-22 fatty acid, lauric acid, palmitic acid, stearic acid, oleic acid, linoleic acid or myristic acid, a silicone, or a mineral oil.

1.12 Any of Compositions 1 or 1.1-1.11, wherein the one or more hydrophobic deposition aids comprise petrolatum (e.g., snow white petrolatum), a vegetable oil (e.g., palm oil, palm kernel oil, coconut oil), a C8-C22 fatty alcohol (e.g., lauryl, stearyl, isostearyl, oleyl, cetyl or myristyl alcohol), a C8-22 fatty acid (e.g, of lauric, palmitic, stearic, oleic, linoleic or myristic acid), or a combination thereof.

1.13 Any of Compositions 1 or 1.1-1.12, wherein the one or more hydrophobic deposition aids comprise white petrolatum or snow white petrolatum, or palm kernel oil, or stearic acid, or isostearyl alcohol, or a combination thereof.

1.14 Any of Compositions 1 or 1.1-1.13, wherein the one or more hydrophobic deposition aids comprise 0.01% to 10% by weight of the composition, e.g., from 0.1% to 10%, or e.g., from 1% to 5%, or e.g., about 1%, 2%, or 4%.

1.15 Composition 1.14, wherein the one or more hydrophobic deposition aids comprise from 0.1% to 10% by weight of the composition.

1.16 Composition 1.14, wherein the one or more hydrophobic deposition aids comprise from 1% to 5% by weight of the composition.

1.17 Composition 1.14, wherein the one or more hydrophobic deposition aids comprise about 1%, or about 2%, or about 4% by weight of the composition.

1.18 Any of Compositions 1 or 1.1-1.17, wherein the weight ratio of phenoxyethanol to deposition aid is from 1:0.25 to 1:5, e.g., 1:0.5 to 1:5, e.g., 1:1 to 1:5, e.g., 1:1 to 1:4, e.g., 1:1 to 1:2, e.g., about 1:0.25, 1:0.5, 1:1, 1:2, 1:3 or 1:4.

1.19 Composition 1.18, wherein the weight ratio of phenoxyethanol to deposition aid is from 1:0.5 to 1:5.

1.20 Composition 1.18, wherein the weight ratio of phenoxyethanol to deposition aid is from 1:1 to 1:5.

1.21 Composition 1.18, wherein the weight ratio of phenoxyethanol to deposition aid is from 1:1 to 1:4.

1.22 Composition 1.18, wherein the weight ratio of phenoxyethanol to deposition aid is from 1:1 to 1:3.

1.23 Composition 1.18, wherein the weight ratio of phenoxyethanol to deposition aid is from 1:1 to 1:2.

1.24 Composition 1.18, wherein the weight ratio of phenoxyethanol to deposition aid is about 1:0.25, or about 1:0.5, or about 1:1, or about 1:2, or about 1:3, or about 1:4, or about 1:5.

1.25 Any of Composition 1 ot 1.1-1.24 further comprising an emulsifier having an HLB of 1 to 4. In certain embodiments, the emulsifier is steareth-2. HLB is the hydrophile lipophile balance. The emulsifier helps the phenoxyethanol stay mixed with the hydrophobic deposition aid.

1.26 Any of Compositions 1 or 1.1-1.25, further comprising an anionic surfactant, cationic surfactant, zwitterionic surfactant, amphoteric surfactant, nonionic surfactant, or a combination thereof.

1.27 Any of Compositions 1 or 1.1-1.26, further comprising inorganic salts, brighteners, perfumes, colorants, sequestering agents, opacifiers, pearlizers, chelating agents (e.g., EDTA), humectants (e.g., polyols, for example, glycerol), or any combination thereof.

1.28 Any of Compositions 1 or 1.1-1.27, wherein the hydrophobic deposition aid enhances the deposition of phenoxyethanol on the skin of the user of the cleansing bar, e.g., results in measurable phenoxyethanol on the skin 24 hours after use.

1.29 Any composition which is the product of the combination of ingredients as identified for Compositions 1 or 1.1-1.28.

1.30 Any foregoing composition, wherein the phenoxyethanol and the hydrophobic deposition aids are pre-mixed, e.g., prior to combination with the soap components, such that the surface of the phenoxyethanol particles is coated with the hydrophobic deposition aids.

1.31 Any foregoing composition wherein the phenoxyethanol is substantially coated by the hydrophobic deposition aids.

The inventors have discovered that the deposition of phenoxyethanol on the skin of consumers using a phenoxyethanol-containing cleansing bar can be enhanced by formulating the bar with a pre-mix of phenoxyethanol and one or more hydrophobic deposition aids. In the absence of these agents, nearly all phenoxyethanol deposited on the user's skin becomes washed away during rinsing with water. However, when the cleansing bar is formulated as described in the present disclosure, the phenoxyethanol can be retained on the skin for long periods of time, providing a long-lasting antibacterial effect.

The hydrophobic deposition aids that are useful for the present disclosure include, but are not limited to, a material having a water solubility less than 1% by weight (solubility is measured at 25° C.), petrolatum, white petrolatum, snow white petrolatum, a vegetable oil, palm oil, palm kernel oil, coconut oil, a seed oil, jojoba oil, jojoba wax, a fat, triglyceride, tallow, shea butter, a glycerol ester of a C8-C22 fatty acid; a glycerol ester of lauric, palmitic, stearic, oleic, linoleic or myristic acid; a C8-C22 fatty alcohol, lauryl alcohol, stearyl alcohol, isostearyl alcohol, oleyl alcohol, cetyl alcohol or myristyl alcohol, a C8-22 fatty acid, lauric acid, palmitic acid, stearic acid, oleic acid, linoleic acid or myristic acid, a silicone, a mineral oil, and combinations thereof. Petrolatum is a complex hydrocarbon mixture. Vegetable oils and fats are mixtures of triglycerides, i.e., tri-glycerol esters of fatty acids. Seed oils, such as jojoba oil, are mixtures of waxes, i.e., the esters of fatty acids with long chain alcohols. Fatty alcohols are the long-chain alcohols derived by reduction of the carboxylic acid group of fatty acids.

In addition to acting as an aid to the deposition of phenoxyethanol on the skin, the deposition aids of the present disclosure also confer benefits of their own, such as, for example, anti-bacterial effects, moisturizing effects, and other skin benefit effects.

In preparing the cleansing bars of the present disclosure, the phenoxyethanol component should be pre-mixed with the hydrophobic deposition aid, e.g., encapsulated by the hydrophobic deposition aid, prior to blending with the other components of the cleansing bar composition. Preferably, the phenoxyethanol and hydrophobic deposition aid are pre-mixed and processed to ensure coating of the surface area of the phenoxyethanol particles by the hydrophobic deposition aid. In a preferred embodiment, the weight ratio of phenoxyethanol to deposition aid is from 1:1 to 1:5, e.g., 1:1 to 1:4, e.g., 1:1 to 1:2, e.g., about 1:1, 1:2, 1:3 or 1:4.

The cleansing bar of the present disclosure includes at least one cleanser component, which can be a soap or a surfactant. In certain embodiments the cleaner component is a hydrophilic soap chip (e.g., "a base component"). Reference is made to U.S. Pat. No. 6,383,999 (Coyle et al.) and U.S. Pat. No. 6,248,703 (Finucane et al.) each of which disclose soap components of a cleansing soap bar. The term "soap" or "soap chip" is used herein in its popular sense, i.e., the alkali metal or alkanol ammonium salts of aliphatic alkane or alkene monocarboxylic acids. Sodium, potassium, mono-, di- and tri-ethanol ammonium cations, or combinations thereof, are suitable for purposes of this invention. In general, sodium soaps are used in the compositions of the present disclosure, but from about 1% to about 25% of the soap may be ammonium, potassium, magnesium, calcium soaps or a mixture of these soaps.

The soap chips useful herein include, but are not limited to, the well known alkali metal salts of aliphatic (alkanoic or alkenoic) acids having about 8 to 22 carbon atoms, preferably 10 to 20 carbon atoms. These may be described as alkali metal carboxylates of alkanoic or alkenoic hydrocarbons having about 12 to about 22 carbon atoms. Soaps having the fatty acid distribution of common vegetable oils may be suitable, e.g., palm kernel oil, palm oil, coconut oil, olive oil or laurel oil, or the fatty acid distribution of tallow (rendered animal fat). The soap may comprise the fatty acid distribution of any combination of natural or synthetic fatty acid sources (e.g., any combination of natural animal or vegetable fats or oils, and/or individual fatty acids).

Any other surfactant can also be present in the soap chip which include but are not limited to sulfate, sulfonate alpha olefin sulfonates, isethionates such as SCl, N-alkyl or N-acyl taurates, sulfosuccinate, phosphates, glycinates, amphoteric surfactants such as betaines, sulfobetaines and the like and nonionic surfactants such as alkanolamide, alkylpolyglycosides and all those surfactants, in general, mentioned in Colgate's U.S. Pat. No. 5,139,781, column 5, line 35 to column 11, line 46.

In one exemplary embodiment, the cleansing bar of this disclosure includes at least about 70% by weight of cleanser active compounds (e.g., soap active compounds).

In an alternate exemplary embodiment, the cleanser component of the composition consists essentially of anionic surfactant, non-ionic surfactants, amphoteric surfactants, cationic surfactants and mixtures thereof.

Optional ingredients can be present in the cleansing bar composition. Non-limiting examples include skin conditioning agents, moisturizing agents, fragrance, dyes and pigments, titanium dioxide, chelating agents such as EDTA, sunscreen active ingredients such as butyl methoxy benzylmethane; antiaging compounds such as alpha hydroxy acids, beta hydroxy acids; antimicrobial materials such as triclocarban, triclosan and the like; preservatives such as hydantoins, imidazolines; polyols such as glycerol, sorbitol, propylene glycol and polyethylene glycols; particulate matter such as silica, talc, or calcium carbonate; antioxidants such as butylated hydroxytoluene (BHT); vitamins such as A, E, K and C; essential oils and extracts thereof such as rosewood and jojoba, particulate matter such as polyethylene beads, jojoba beads, lufa, or oat flour, and mixtures of any of the foregoing components.

In one embodiment the cleansing bar includes fragrance in an amount of about 0.001% to about 2% by weight of the composition.

In one embodiment the cleansing bar includes pearlizers, such as titanium dioxide, in an amount of about 0.01% to 1% by weight.

In one embodiment the cleansing bar includes one or more pigments, such as chromium oxide green, in an amount of about 0.001% to about 1% by weight.

In one embodiment, the cleansing bar includes silica, or silicon dioxide, incorporated at a level of from about 0.1% to about 15%, preferable from about 1% to about 10%, more preferably from about 3% to about 7%. Silica is available in a variety of forms, including but not limited to, crystalline, amorphous, fumed, precipitated, gel, and colloidal forms.

In one embodiment, the cleansing bar includes free fatty acids to provide enhanced skin feel benefits, such as softer or smoother feeling skin. Suitable free fatty acids include those derived from tallow, coconut oil, palm oil and palm kernel oil.

In a second exemplary embodiment, the invention includes a method (Method 1) of increasing the deposition of phenoxyethanol on the skin by a cleansing bar, comprising the step of combining phenoxyethanol with one or more hydrophobic deposition aids to form a mixture, adding the resulting mixture to at least one cleanser chosen from soap and surfactant, and forming therefrom a cleansing bar.

The present disclosure provides additional exemplary embodiments, including 1.1 Method 1, wherein the phenoxyethanol is substantially coated by the hydrophobic stabilizing agent.
1.2 Any foregoing Method, wherein the combining the phenoxyethanol and the hydrophobic deposition aid further comprises an emulsifier having an HLB of 1 to 4. The emulsifier helps the phenoxyethanol stay mixed with the hydrophobic deposition aid.
1.3 Method 1.2 wherein the emulsifier is steareth-2.
1.4 Any foregoing Method, wherein the phenoxyethanol comprises from 0.01% to 2% by weight of the composition, e.g., from 0.1% to 1.5%, or e.g., from 0.5% to 1%, or e.g., about 1%.
1.5 Any foregoing Method, wherein the phenoxyethanol comprises from 0. ° 1% to 1.5% by weight of the composition.
1.6 Any foregoing Method, wherein the phenoxyethanol comprises from 0.5% to 1% by weight of the composition.
1.7 Any foregoing Method, wherein the phenoxyethanol comprises about 1% by weight of the composition.
1.8 Any foregoing Method, wherein the cleansing bar comprises one or more soap components, for example, an alkali metal (e.g., sodium or potassium) or alkylammonium (e.g., mono-, di- or tri-ethanol ammonium) salt of a carboxylic acid.
1.9 Any foregoing Method, wherein the one or more soap components comprise an alkali metal (e.g., sodium or potassium) or alkylammonium salt of a fatty acid, e.g., a C8-22 saturated or unsaturated fatty acid, preferably a C10-20 saturated or unsaturated fatty acid.
1.10 Any of Methods 1 or 1.1-1.6, wherein the one or more soap components comprise an alkali metal salt (e.g., sodium or potassium) or alkylammonium salt of a C8-22 carboxylic acid.
1.11 Any foregoing Method, wherein the one or more soap components comprise the alkali metal (e.g., sodium or potassium) or alkylammonium salts of the fatty acids present in a natural vegetable oil, e.g., palm kernel oil, palm oil, coconut oil, olive oil or laurel oil, or in tallow (rendered animal fat).
1.12 Any foregoing Method, wherein the one or more soap components comprise the alkali metal salt (e.g., sodium or potassium) of palm oil or coconut oil.
1.13 Any foregoing Method, wherein the one or more soap components comprise from about 30, 40, 50 or 60% by weight of the composition to about 70, 80, 85, 90 or 95% by weight of the composition.
1.14 Any foregoing Method, wherein the one or more hydrophobic deposition aids comprise at least one material chosen from a material having a water solubility less than 1% by weight, petrolatum, white petrolatum, snow white petrolatum, a vegetable oil, palm oil, palm kernel oil, coconut oil, a seed oil, jojoba oil, jojoba wax, a fat, triglyceride, tallow, shea butter, a glycerol ester of a C8-C22 fatty acid; a glycerol ester of lauric, palmitic, stearic, oleic, linoleic or myristic acid; a C8-C22 fatty alcohol, lauryl alcohol, stearyl alcohol, isostearyl alcohol, oleyl alcohol, cetyl alcohol or myristyl alcohol, a C8-22 fatty acid, lauric acid, palmitic acid, stearic acid, oleic acid, linoleic acid or myristic acid, a silicone, or a mineral oil.
1.15 Any foregoing Method, wherein the one or more hydrophobic deposition aids comprise petrolatum (e.g., white petrolatum or snow white petrolatum), a vegetable oil (e.g., palm oil, palm kernel oil, coconut oil), a C8-C22 fatty alcohol (e.g., lauryl, stearyl, isostearyl, oleyl, cetyl or myristyl alcohol), a C8-22 fatty acid (e.g, of lauric, palmitic, stearic, oleic, linoleic or myristic acid), or a combination thereof.

1.16 Any foregoing Method, wherein the one or more hydrophobic deposition aids comprise white petrolatum or snow white petrolatum, or palm kernel oil, or stearic acid, or isostearyl alcohol, or a combination thereof.

1.17 Any foregoing Method, wherein the one or more hydrophobic deposition aids comprise 0.01% to 10% by weight of the composition, e.g., from 0.1% to 10%, or e.g., from 1% to 5%, or e.g., about 1%, 2%, or 4%.

1.18 Any foregoing Method, wherein the one or more hydrophobic deposition aids comprise from 0.1% to 10% by weight of the composition.

1.19 Any foregoing Method, wherein the one or more hydrophobic deposition aids comprise from 1% to 5% by weight of the composition.

1.20 Any foregoing Method, wherein the one or more hydrophobic deposition aids comprise about 1%, or about 2%, or about 4% by weight of the composition.

1.21 Any foregoing Method, wherein the weight ratio of phenoxyethanol to deposition aid is from 1:0.25 to 1:5, e.g., 1:0.5 to 1:5, e.g., 1:1 to 1:5, e.g., 1:1 to 1:4, e.g., 1:1 to 1:2, e.g., about 1:0.25, 1:0.5, 1:1, 1:2, 1:3 or 1:4.

1.22 Any foregoing Method, wherein the weight ratio of phenoxyethanol to deposition aid is from 1:0.5 to 1:5.

1.23 Any foregoing Method, wherein the weight ratio of phenoxyethanol to deposition aid is from 1:1 to 1:5.

1.24 Any foregoing Method, wherein the weight ratio of phenoxyethanol to deposition aid is from 1:1 to 1:4.

1.25 Any foregoing Method, wherein the weight ratio of phenoxyethanol to deposition aid is from 1:1 to 1:3.

1.26 Any foregoing Method, wherein the weight ratio of phenoxyethanol to deposition aid is from 1:1 to 1:2.

1.27 Any foregoing Method, wherein the weight ratio of phenoxyethanol to deposition aid is about 1:0.25, or about 1:0.5, or about 1:1, or about 1:2, or about 1:3, or about 1:4, or about 1:5.

1.28 Any foregoing Method, further comprising an anionic surfactant, cationic surfactant, zwitterionic surfactant, amphoteric surfactant, nonionic surfactant, or a combination thereof.

1.29 Any foregoing Method, further comprising inorganic salts, brighteners, perfumes, colorants, sequestering agents, opacifiers, pearlizers, chelating agents (e.g., EDTA), humectants (e.g., polyols, for example, glycerol) or any combination thereof.

1.30 Any foregoing Method, wherein the hydrophobic deposition aid enhances the deposition of phenoxyethanol on the skin of the user of the cleansing bar, e.g., results in measurable phenoxyethanol on the skin 24 hours after use.

1.31 Any foregoing Method, wherein the phenoxyethanol and the hydrophobic deposition aid are pre-mixed together, e.g., prior to being combined with any aqueous or hydrophilic soap components.

1.32 Any foregoing Method, wherein the hydrophobic deposition aid is heated to or above its melting point before it is combined with the phenoxyethanol.

1.33 Any foregoing Method, wherein the phenoxyethanol is substantially coated by the hydrophobic deposition aid.

1.34 Any foregoing Method, wherein the pre-mixture of phenoxyethanol and the hydrophobic deposition aid is then blended with soap chips, and any other optional components of the final cleansing bar composition.

1.35 Any foregoing Method, further comprising the step of adding additional optional ingredients to the blended phenoxyethanol/hydrophobic deposition aid and soap mixture.

1.36 Any foregoing Method, further comprising the processing of the final composition to produce cleansing bars.

1.37 Any foregoing Method, wherein the product cleansing bars consist essentially of any one of Compositions 1 or 1.1-1.30.

1.38 A cleansing bar which is prepared by any of Methods 1 or 1.1-1.37.

The cleansing bars of the present disclosure may be prepared by any of the techniques known to those skilled in the art, including both batch processes and continuous processes. The first step in the preparation of the cleansing bar is the preparation of the soap component. Techniques known to those skilled in the art may be used, such as the classic kettle boiling process or the modern continuous soap manufacturing process. For example, an appropriate fat, oil, or carboxylic acid, or mixture thereof, is first combined with a base (e.g., sodium or potassium hydroxide or carbonate) in the presence of water to form the soap component. The soap component can then be processed and purified to remove excess base and/or glycerol as needed, and formed into chips, pellets, noodles or other solid or semi-solid forms. Optional ingredients such as additional surfactants may also be added after the removal of excess base but before formation into chips, pellets or noodles. The soap component may then be ground up, suspended in water and combined with the phenoxyethanol and hydrophobic deposition aid, as well as other optional additives. The phenoxyethanol and hydrophobic deposition aids are pre-mixed, with melting of the hydrophobic deposition aid, if necessary, before addition to the soap mixture. The phenoxyethanol pre-mix is processed, as by stirring or grinding to promote an even coating of the phenoxyethanol particles by the hydrophobic deposition aid. The resulting mixture is then blended, with heating if necessary, with the soap chips and any other desired ingredients. After blending, the final composition is then formed into the finished cleansing bar product.

The cleansing bar may be formed by the extrusion method, and may be of varying sizes and shapes such as ovoid or rectangular in shape with either a flat or curved profile as an overall appearance.

EXAMPLES

Exemplary embodiments of the present disclosure will be illustrated by reference to the following examples, which are included to exemplify, but not to limit the scope of the present invention.

In the examples and elsewhere in the description of the invention, chemical symbols and terminology have their usual and customary meanings. Temperatures are in degrees Celsius unless otherwise indicated. The amounts of the components are in weight percents based on the standard described; if no other standard is described then the total weight of the composition is to be inferred. Various names of chemical components include those listed in the CTFA International Cosmetic Ingredient Dictionary (Cosmetics, Toiletry and Fragrance Association, Inc., 7$^{th}$ ed. 1997).

Example 1: Analysis of Deposition Effect

Pre-mixes of phenoxyethanol with five deposition aids are prepared: (a) palm kernel oil, (b) stearic acid, (c) petrolatum, (d) isostearyl alcohol, and (e) water (as a control). The weight ratio of phenoxyethanol to deposition aid is either 1:1, 2:1 or 4:1. Stearic acid is melted at 80-100° C. prior to addition of phenoxyethanol. Palm kernel oil is melted at 50° C. prior to addition of phenoxyethanol. Petrolatum is combined with phenoxyethanol at room temperature, then heated to a liquid. Isostearyl alcohol or water is combined with phenoxyethanol at room temperature. A soap slurry is then prepared by combining super fat soap chips and water in a 1:0.15 weight ratio with gentle heating and vigorous stirring. Each pre-mix is combined with soap slurry and mixed in a pestle and mortar, to obtain a composition containing 1% by weight of phenoxyethanol, and the mixture is formed into a bar or ball.

Two inch by two inch squares of Vitro-Skin (in vitro skin model) are prepared for testing by incubating in a close, controlled-humidity chamber for 16 to 24 hours. Each hydrated Vitro-Skin sample is then dipped for 5-10 seconds in 40° C. deionized water then placed on a clean plastic surface. With gloved hands, each sample cleansing bar composition is rotated 10 times under running 35° C. tap water. Residual water is allowed to drain off the bar, then the wetted bar is applied for 15 seconds against the Vitro-Skin with minimal force. The bar is then set aside, and with a gloved index finger, the Vitro-Skin is messaged with the index finger for 45 seconds (to simulate lathering). The Vitro-skin is then quickly rinsed for 15 seconds with room temperature deionized water using a nozzle stream of water. The Vitro-Skin is allowed to air-dry for 3-4 hours, and then is analyzed by HPLC for the presence of phenoxyethanol. Briefly, dried Vitro-Skin samples are incubated for 24-48 hours in ethanol to extract the phenoxyethanol, the ethanol solutions are evaporated and then reconstituted in appropriate solvent for HPLC analysis.

Each Vitro-Skin sample is analyzed for phenoxyethanol content, and the values are normalized to the control composition. The results are shown in Table 1.

| Deposition Improvement Compared to Control | | | |
| --- | --- | --- | --- |
| | 1:1 Ratio | 2:1 Ratio | 4:1 Ratio |
| Isostearyl Alcohol | 11% | 18% | 28% |
| Palm Kernel Oil | 35% | 14% | 41% |
| Petrolatum | 30% | 130% | 45% |
| Stearic Acid | 34% | 32% | 22% |

Deposition Improvement is calculated as (PE=phenoxyethanol):

$$D.I. = \frac{(PE \text{ content with deposition aid}) - (PE \text{ content of control})}{(PE \text{ content of control})} \times 100\%$$

The results demonstrate a significant improvement in phenoxyethanol deposition when hydrophobic deposition aids are pre-mixed with phenoxyethanol during cleansing bar manufacture. Compositions containing palm kernel oil, petrolatum and stearic acid each show more than 30% greater skin deposition of phenoxyethanol compared to the skin deposition of phenoxyethanol achieved by the control. The strongest effect is seen for petrolatum at a 2:1 ratio (130% increase in deposition compared to control).

Example 2: Cleansing Bar Composition

Table 2 shows an exemplary base compositions according to the present disclosure. Each base composition can be optionally combined with additional ingredients to formulate a final cleansing bar. For example, water, fragrances, fillers and other ingredients disclosed hereinabove can be added.

| Material | Range | Formula A | Formula B |
| --- | --- | --- | --- |
| Sodium Soap Chips | 80-99.8% | 98% | 90% |
| Phenoxyethanol | 0.01-2% | 1% | 1% |
| Deposition aid | 0.1-10% | | |
| Snow White Petrolatum | | 1% | |
| Palm Kernel Oil | | | 1% |

What is claimed is:

1. A cleansing bar composition comprising:
   a) at least one cleanser chosen from soap and surfactant;
   b) phenoxyethanol; and
   c) one or more hydrophobic deposition aids,
   wherein the phenoxyethanol is coated by the hydrophobic deposition aid by premixing the phenoxyethanol with the hydrophobic deposition aid, wherein the composition is a solid cleansing bar,
   wherein the hydrophobic deposition aid comprises at least one material chosen from a material having a water solubility less than 1% by weight, petrolatum, white petrolatum, snow white petrolatum, a vegetable oil, palm oil, palm kernel oil, coconut oil, a seed oil, jojoba oil, jojoba wax, a fat, triglyceride, tallow, shea butter, a glycerol ester of a C8-C22 fatty acid; a glycerol ester of lauric, palmitic, stearic, oleic, linoleic or myristic acid; a C8-C22 fatty alcohol, lauryl alcohol, stearyl alcohol, isostearyl alcohol, oleyl alcohol, cetyl alcohol or myristyl alcohol, a C8-22 fatty acid, lauric acid, palmitic acid, stearic acid, oleic acid, linoleic acid or myristic acid, a silicone, or a mineral oil, and
   wherein the composition exhibits at least 11% Deposition Improvement (D.I.), wherein said D.I. is calculated as (PE=phenoxyethanol, and control=water):

$$D.I. = \frac{(PE \text{ content with deposition aid}) - (PE \text{ content of control})}{(PE \text{ content of control})} \times 100\%.$$

2. The composition of claim 1, wherein the phenoxyethanol is present in an amount of 0.01% to 2% by weight of the composition.

3. The composition of claim 1, wherein the hydrophobic deposition aid comprises 0.1% to 10% by weight of the composition.

4. The composition of claim 1, wherein the weight ratio of phenoxyethanol to hydrophobic deposition aid is 1:0.25 to 1:5.

5. The composition of claim 1, wherein the weight ratio of phenoxyethanol to hydrophobic deposition aid is 1:1 to 1:2.

6. The composition of claim 1, wherein the at least one cleanser comprises a soap.

7. The composition of claim 1 further comprising an emulsifier having an HLB of 1 to 4.

8. The composition of claim 7, wherein the emulsifier is steareth-2.

9. A method of increasing phenoxyethanol deposition by a cleansing bar comprising:
   a) combining phenoxyethanol in a hydrophobic deposition aid to form a mixture, and coating the phenoxyethanol with the hydrophobic deposition aid by premixing the phenoxyethanol with the hydrophobic deposition aid;
b) adding the mixture to at least one cleanser chosen from soap and surfactant; and
c) forming a cleansing bar;
wherein the hydrophobic deposition aid comprises at least one material chosen from a material having a water solubility less than 1% by weight, petrolatum, white petrolatum, snow white petrolatum, a vegetable oil, palm oil, palm kernel oil, coconut oil, a seed oil, jojoba oil, jojoba wax, a fat, triglyceride, tallow, shea butter, a glycerol ester of a C8-C22 fatty acid; a glycerol ester of lauric, palmitic, stearic, oleic, linoleic or myristic acid; a C8-C22 fatty alcohol, lauryl alcohol, stearyl alcohol, isostearyl alcohol, oleyl alcohol, cetyl alcohol or myristyl alcohol, a C8-22 fatty acid, lauric acid, palmitic acid, stearic acid, oleic acid, linoleic acid or myristic acid a silicone or a mineral oil.

10. The method of claim 9, wherein combining the phenoxyethanol and the hydrophobic deposition aid comprises adding an emulsifier having an HLB of 1 to 4.

11. The method of claim 10, wherein the emulsifier is steareth-2.

12. The method of claim 9, wherein the phenoxyethanol is present in an amount of 0.01% to 2% by weight of the composition.

13. The method of claim 9, wherein the hydrophobic deposition aid comprises 0.1% to 10% by weight of the composition.

14. The method of claim 9, wherein the weight ratio of phenoxyethanol to hydrophobic deposition aid is 1:0.25 to 1:5.

15. The method of claim 9, wherein the at least one cleanser comprises a soap.

16. The method of claim 9, wherein the hydrophobic deposition aid enhances the deposition of phenoxyethanol on the skin of the user of the cleansing bar, and wherein the hydrophobic deposition aid results in measurable phenoxyethanol on the skin of the user 24 hours after use of the cleansing bar.

* * * * *